United States Patent
Clark et al.

(10) Patent No.: US 9,192,317 B2
(45) Date of Patent: *Nov. 24, 2015

(54) IMPLANTABLE ACTIVE FIXATION LEAD WITH BIODEGRADABLE HELICAL TIP

(71) Applicant: Cardiac Pacemakers, Inc., St. Paul, MN (US)

(72) Inventors: Bryan A. Clark, Forest Lake, MN (US); Thomas J. Herbst, Coon Rapids, MN (US); Kimberly A. Jorgensen, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/546,607

(22) Filed: Nov. 18, 2014

(65) Prior Publication Data

US 2015/0073248 A1 Mar. 12, 2015

Related U.S. Application Data

(63) Continuation of application No. 13/295,445, filed on Nov. 14, 2011, now Pat. No. 8,923,985.

(60) Provisional application No. 61/432,812, filed on Jan. 14, 2011.

(51) Int. Cl.
*A61N 1/05* (2006.01)
*A61B 5/042* (2006.01)

(52) U.S. Cl.
CPC .............. *A61B 5/042* (2013.01); *A61N 1/059* (2013.01); *A61N 1/0573* (2013.01); *Y10T 29/49204* (2015.01); *Y10T 29/49208* (2015.01)

(58) Field of Classification Search
None
See application file for complete search history.

(56) References Cited

U.S. PATENT DOCUMENTS

| | | | |
|---|---|---|---|
| 4,628,944 A | 12/1986 | MacGregor et al. |
| 5,425,755 A | 6/1995 | Doan |
| 5,716,391 A | 2/1998 | Grandjean |
| 5,776,178 A | 7/1998 | Pohndorf et al. |
| 6,842,649 B2 | 1/2005 | Laabs et al. |
| 6,863,671 B1 | 3/2005 | Strobel et al. |
| 7,027,876 B2 | 4/2006 | Casavant et al. |
| 2005/0119718 A1 | 6/2005 | Coe et al. |
| 2005/0251240 A1 | 11/2005 | Doan |
| 2006/0235499 A1 | 10/2006 | Heil, Jr. et al. |
| 2007/0043414 A1 | 2/2007 | Fifer et al. |
| 2012/0185023 A1 | 7/2012 | Clark et al. |

FOREIGN PATENT DOCUMENTS

| | | |
|---|---|---|
| DE | 102004035903 A1 | 2/2006 |
| JP | 6205842 A | 7/1994 |
| JP | 9225042 A | 9/1997 |

OTHER PUBLICATIONS

International Search Report and Written Opinion issued in PCT/US2001/060594, mailed_Feb. 6, 2012, 9 pages.

*Primary Examiner* — Erica Lee
(74) *Attorney, Agent, or Firm* — Faegre Baker Daniels LLP

(57) ABSTRACT

Described is an implantable medical device comprising housing having a distal end and a proximal end, the proximal end fixedly coupled to the distal end of the lead body, a coupler rotatably disposed within the housing, the coupler having a proximal end and a distal end, and a helical electrode fixedly secured to the distal end of the coupler. The helical electrode comprises a proximal axial length portion that comprises a non-degradable material, and a distal axial length portion that comprises a biodegradable material. The proximal and distal portions may include concave/convex surfaces or threaded portions. The coupler and the helical electrode are configured to rotate and therefore translate relative to the housing.

20 Claims, 8 Drawing Sheets

IMPLANTABLE ACTIVE FIXATION LEAD WITH BIODEGRADABLE HELICAL TIP

RELATED APPLICATION

This application is a continuation of U.S. application Ser. No. 13/295,445, entitled "IMPLANTABLE ACTIVE FIXATION LEAD WITH BIODEGRADABLE HELICAL TIP", filed Nov. 14, 2011 which is now U.S. Pat. No. 8,923,985, issued Dec. 30, 2014, which claims priority to U.S. Provisional Application No. 61/432,812, entitled "IMPLANTABLE ACTIVE FIXATION LEAD WITH BIODEGRADABLE HELICAL TIP", filed on Jan. 14, 2011, each of which is commonly owned and is incorporated herein by reference in its entirety.

TECHNICAL FIELD

The present invention relates to implantable medical devices and relates more particularly to leads used with implantable medical devices for cardiac rhythm management (CRM) systems.

BACKGROUND

Various types of medical electrical leads for use in CRM and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site acutely, post-implant while normal processes of peri-tip wound healing and tissue ingrowth have time to occur.

SUMMARY

In Example 1, an implantable lead including a flexible body extending between a proximal end and a distal end, and a distal assembly coupled to the distal end of the body. The distal assembly includes a housing having a distal end and a proximal end, the proximal end fixedly coupled to the distal end of the lead body, a coupler rotatably disposed within the housing, the coupler having a proximal end and a distal end, and a helical electrode fixedly secured to the distal end of the coupler. The helical electrode includes a proximal axial length portion that comprises a non-degradable material, and a distal axial length portion that comprises a biodegradable material, wherein the coupler and the helical electrode are configured to translate relative to the housing between fully extended and fully retracted positions.

In Example 2, the lead according to Example 1, wherein the helix assembly is configured such that the biodegradable portion and at least a portion of the non-biodegradable portion of the helix extend beyond the distal end of the housing when the helix assembly is extended.

In Example 3, the lead according to Example 1 or 2, wherein the distal axial length portion comprises a sharp distal tip for penetrating tissue.

In Example 4, the lead according to Examples 1-3, wherein the proximal axial length portion comprises a blunt distal end.

In Example 5, the lead according to Examples 1-4, wherein the helical electrode further comprises an interface between a distal end of the proximal axial length portion and a proximal end of the distal axial length portion.

In Example 6, the lead according to Examples 1-5, wherein the distal end of the proximal axial length portion comprises a convex surface and the proximal end of the distal axial length portion comprises a concave surface that is complementary to the convex surface.

In Example 7, the lead according to Examples 1-6, wherein the distal end of the proximal axial length portion comprises a plurality of threads and the proximal end of the distal axial length portion comprises a surface that is complementary to the threads.

In Example 8, the lead according to Examples 1-7, wherein the proximal end of the distal axial length portion comprises a plurality of threads and the distal end of the proximal axial length portion comprises a surface that is complementary to the threads.

In Example 9, the lead according to Examples 1-8, wherein the distal end of the proximal axial length portion comprises a male-shaped engagement member and the proximal end of the distal axial length portion comprises a female-shaped engagement member.

In Example 10, the lead according to Examples 1-9, wherein the proximal end of the distal axial length portion comprises a male-shaped engagement member and the distal end of the proximal axial length portion comprises a female-shaped engagement member.

In Example 11, the lead according to Examples 1-10, wherein at the interface, the proximal axial length portion and the distal axial length portion are adhered to one another.

In Example 12, the lead according to Examples 1-11, wherein when the helical electrode is in a fully extended position, a portion of the helical electrode extends exterior and distal to the housing and has a length of about 0.025 inches to about 0.150 inches.

In Example 13, the lead according to Examples 1-12, wherein the distal axial length portion of the helical electrode has a length of about 0.005 inches to about half of length of the portion of the helical electrode that extends exterior and distal to the housing, and the proximal axial length portion has a length of about half of the length of the portion of the helical electrode that extends exterior and distal to the housing to about 0.145 inches.

In Example 14, the lead according to Examples 1-13, wherein the helical electrode comprises an outer diameter of about 0.025 inches to about 0.075 inches.

In Example 15, the lead according to Examples 1-14, wherein the helical electrode comprises a wire comprising a cross-sectional diameter of about 0.005 inches to about 0.020 inches.

In Example 16, the lead according to Examples 1-15, wherein either one or both of the proximal axial length portion and the distal axial length portion is electrically conductive.

In Example 17, a method of making an electrically active helix for a lead, including the steps of: a) forming an elongated helix body precursor having a proximal end and a distal end, said helix body precursor comprises a proximal axial length portion comprising a non-degradable material and a distal axial length portion comprising a biodegradable material; and b) forming said helix body precursor into a helix body in which a plurality of helical revolutions are formed between said proximal end and said distal end of said helix body precursor.

In Example 18, a method of making a fixation helix for a lead, comprising the steps of: a) forming a first helical body having a proximal and a distal end between which a plurality of helical revolutions are formed, wherein the first helical body comprises a non-degradable material; b) forming a second helical body having a proximal and a distal end between which a plurality of helical revolutions are formed, wherein the second helical body comprises a biodegradable material; and c) joining the proximal end of the second helical body to the distal end of the first helical body.

In Example 19, the method of Example 18, wherein the steps of forming the first and second helical bodies include forming the distal end of the first helical body and the proximal end of the second helical body to have complementary surfaces.

In Example 20, the method of Examples 18-19, wherein the step of forming the first helical body includes forming a blunt distal end, and the step of forming the second helical body includes forming a sharp distal tip for penetrating tissue.

In Example 21, a method of making an electrically active helix for a lead, comprising the steps of: a) forming an elongated tube of biodegradable material having first and second ends; b) forming an elongated tube of non-degradable material having first and second ends; c) attaching the first end of the biodegradable tube to the first end of the non-degradable tube to form a combined tube; and d) cutting the combined tube into the shape of a helix.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
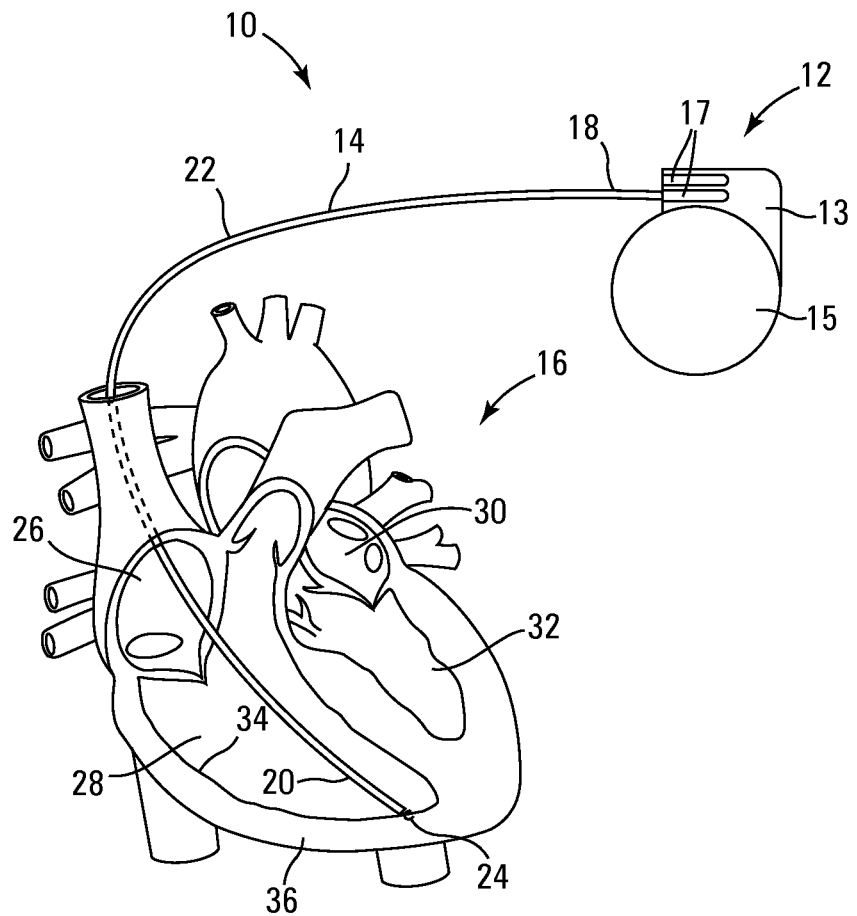
FIG. 1 is a combined cutaway of a heart and a perspective view of an implantable medical device and lead in accordance with one embodiment.

While the invention is amenable to various modifications and alternative forms, specific embodiments have been shown by way of example in the drawings and are described in detail herein. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical device (IMD) 10. The IMD 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body, or flexible body, 22 extending from the proximal region 18 to the distal region 20. The proximal region 18 is coupled to the pulse generator 12 and the distal region 20 is coupled to the heart 16. The distal region 20 includes an extendable/retractable fixation helix 24. The fixation helix 24 locates and/or secures the distal region 20 of the lead 14 within the heart 16. The fixation helix 24 comprises a distal portion and a proximal portion, wherein at least a portion of the distal portion comprises a biodegradable portion, which will be discussed in greater detail elsewhere. The biodegradable portion may degrade or be resorbed after a period of time has passed after implantation of the lead 14 within the heart 16.

The pulse generator 12 typically includes a connector header 13 that couples the pulse generator 12 to the lead 14. The connector header 13 typically contains one or more bores 17 that is/are able to receive a connector(s) (not shown) that is/are part of a connector assembly (not shown, but see 40 in FIG. 2, discussed herein) formed near the proximal region 18 of the lead 14, wherein electrical contacts (not shown) of the header 13 couple with lead contacts (not shown) of the connector assembly (not shown).

The header 13 is attached to a hermetically sealed enclosure 15 that contains a battery, electronic circuitry, and other components known to those skilled in the art. Electrical contacts (not shown) in the header 13 are any type known to those skilled in the art that are electrically connected via feedthroughs (not shown) mounted to extend through the hermetically sealed enclosure 15 in order to electrically couple the lead 14 with pulse generator 12.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to a patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 of the lead 14 can be made from any flexible, biocompatible material suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body 22 characteristics to its intended clinical and operating environments. In various embodiments, proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes a thin inner lining tissue of endocardium 34 covering the thicker, muscular myocardium 36. In some embodiments as illustrated, the fixation helix 24, located at the distal region 20 of the lead, penetrates through the endocardium 34, and is imbedded within the myocardium 36. In one embodiment, the IMD 10 includes a plurality of leads 14. For example, it may include a first lead 14 adapted to convey electrical signals between the pulse generator 12 and the right ventricle 28, and a second lead (not shown) adapted to convey electrical signals between the pulse generator 12 and the right atrium 26. Additional leads, e.g., one or more coronary venous leads (not shown) for stimulating a left atrium 30 and/or a left ventricle 32, may also be employed.

In the illustrated embodiment shown in FIG. 1, the fixation helix 24 penetrates the endocardium 34 of the right ventricle 28 and is imbedded in the myocardium 36 of the heart 16. In some embodiments, the fixation helix 24 is electrically active and thus can be used to sense the electrical activity of the heart 16 or to apply a stimulating pulse to the right ventricle 28. This type of fixation helix 24 is also known as a "tip electrode," and is generally a low-voltage electrode. In other embodiments, the fixation helix 24 is not electrically active. Rather, in some embodiments, other components of the lead 14 are electrically active.

Figure 2:
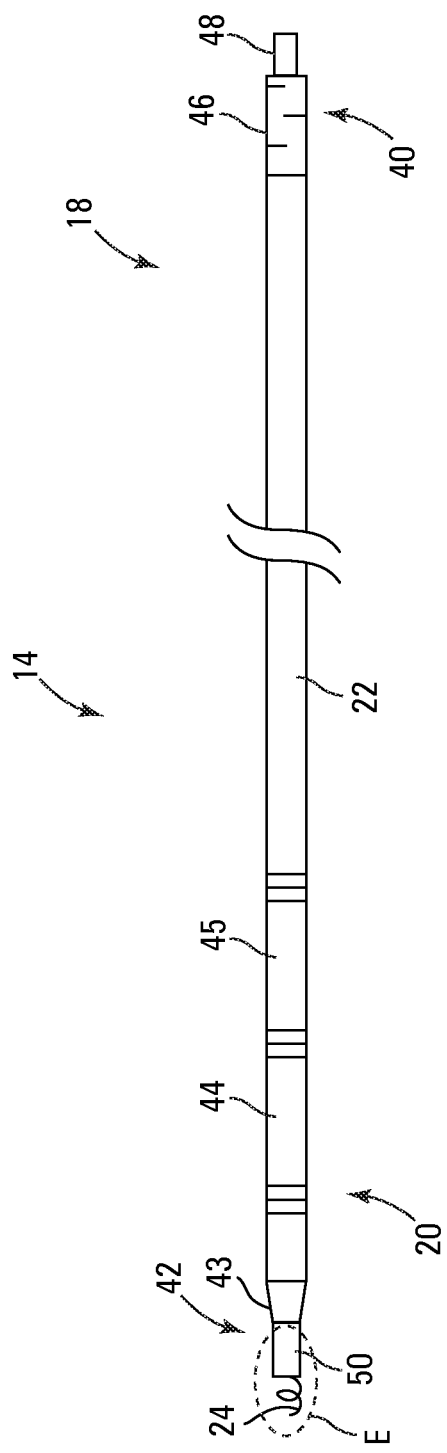
FIG. 2 is a side elevation view of the lead of FIG. 1.

FIG. 2 is an isometric illustration of an embodiment of the lead 14. A connector assembly 40 is disposed at or near the proximal region 18 of the lead 14. The connector assembly 40 includes a connector 46 and a terminal pin 48. The connector 46 is configured to be coupled to the lead body 22 and is configured to mechanically and electrically couple the lead 14 to the header 13 on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture (not shown) extending therethrough in order to accommodate a guide wire or an insertion stylet.

A distal assembly 42 is disposed at or near the distal region 20 or distal end of the lead 14 or lead body 22. Depending on the functional requirements of the IMD 10 (see FIG. 1) and the therapeutic needs of a patient, the distal region 20 of the lead 14 may include one or more electrodes. In the illustrated embodiment, the distal region 20 includes a single coil electrode, otherwise referred to as a "high-voltage electrode," or a pair of such coil electrodes 44 and 45, as shown, that can function as shocking electrodes for providing a defibrillation shock to the heart 16. In some embodiments, coil electrodes 44 and 45 include a coating that is configured to control (i.e., promote or discourage) tissue ingrowth. In various embodiments, the lead 14 may include only a single coil electrode. In various other embodiments, the lead 14 also includes one or more low-voltage electrodes (e.g., ring electrodes), such as electrode 43, along the lead body 22 in lieu of or in addition to the coil electrodes 44, 45. When present, the low-voltage electrodes operate as relatively low-voltage, pace/sense electrodes. As will be appreciated by those skilled in the art, a wide range of electrode combinations may be incorporated into the lead 14 within the scope of the various embodiments.

In some embodiments, and as shown in FIG. 2, the distal region 20 of the lead 14 may include an additional low-voltage (e.g., ring) electrode 43 between the distal-most shocking coil 44 and the distal assembly 42. Such a lead is a tri-polar lead because it is configured with a tip electrode (i.e., the fixation helix 24), a ring electrode 43 and a coil electrode 44 (actually includes two coil electrodes 44, 45), or is otherwise known as a "dedicated bipolar lead."

The distal assembly 42 includes a housing 50, within which the fixation helix 24, or helical electrode, is at least partially disposed. As will be explained in greater detail herein, the housing 50 accommodates a mechanism that enables the fixation helix 24 to move distally and proximally relative to the housing 50, and that structure (not seen in this view) may limit distal travel of the fixation helix 24 (relative to the housing 50) in order to reduce or prevent over-extension of the fixation helix 24. As noted above, the fixation helix 24 operates as an anchoring means for anchoring the distal region 20 of the lead 14 within the heart 16.

In some embodiments, the fixation helix 24, or helical electrode, is electrically active, and is used as a low-voltage, pace/sense electrode. In some embodiments, the fixation helix 24 is made at least in part of an electrically conductive material such as ELGILOY™, MP35N™, tungsten, tantalum, iridium, platinum, titanium, palladium, stainless steel as well as alloys of any of these materials. In some embodiments, the fixation helix 24 is made at least in part of a non-electrically conductive material such as polyethersulfone (PES), polyurethane-based thermoplastics, ceramics, polyetheretherketone (PEEK) and polypropylene.

Figure 3:
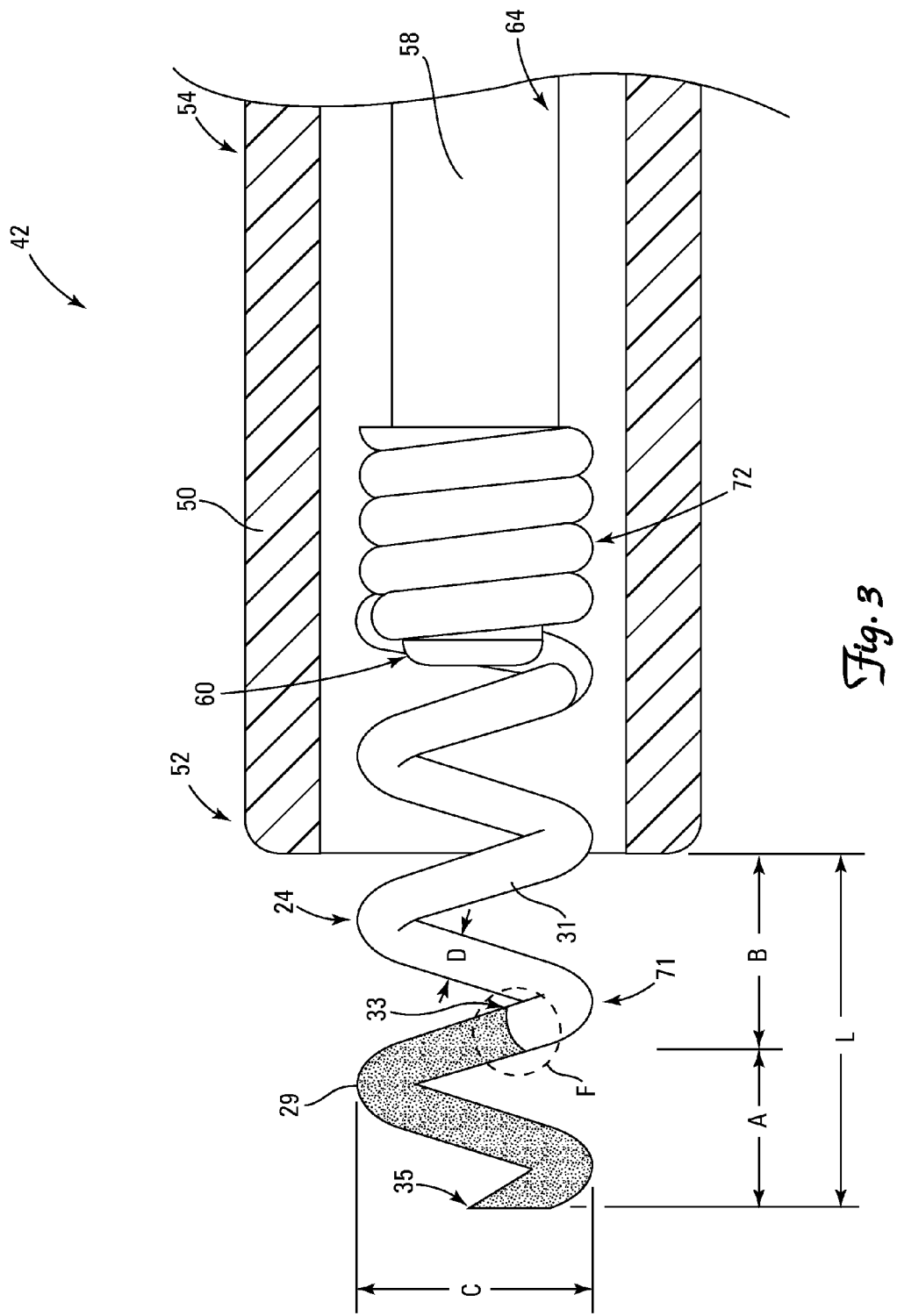
FIG. 3 is a partial cross-sectional view of the lead of FIG. 1 at E in FIG. 2 and shown in an extended position.

FIG. 3 illustrates a partial cross-section of a portion of the lead 14. In FIG. 3, the fixation helix 24 is illustrated in an extended position. As shown, in the extended position, the helix assembly is configured so that a distal, biodegradable portion 29 and at least part of a proximal, non-biodegradable portion 31 of the helix 24 extend beyond the distal tip 52 of the housing 50 (i.e., the distal extremity of the lead 14) when fully extended. In the illustrated embodiment, the fixation helix 24 is electrically active so as to be operable as a low-voltage, pace/sense electrode.

As shown in FIG. 3, the housing 50 includes a distal region 52 and a proximal region 54. The proximal region 54 of the housing 50, in one embodiment, is fixedly coupled to the distal end 20 of the lead body 22 (FIG. 2). In various embodiments, the housing 50 is generally rigid or semi-rigid. In some embodiments, the housing 50 is made of an electrically conductive material such as ELGILOY™, MP35N™, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

As shown, the distal assembly 42 includes a coupler 58. In some embodiments, the coupler 58 is formed of a metallic material and is disposed within the housing 50 and configured to move longitudinally and/or rotationally with respect to the housing 50. The coupler 58 includes a distal portion 60 and a proximal portion 64. In some embodiments, the proximal portion 64 of the coupler 58 is connected to a conductor member (not shown). The fixation helix 24 is connected to the distal portion 60 of the coupler 58.

The fixation helix 24 has a distal region 71 and a proximal region 72. As shown in the embodiment of FIG. 3, the proximal region 72 is secured to the distal portion 60 of the coupler 58. One or more attachment methods are used to secure the fixation helix 24 to the coupler 58. In some embodiments, the proximal region 72 of the fixation helix 24 is welded or soldered onto the distal portion 60 of the coupler 58. In some embodiments, the proximal region 72 of the fixation helix 24 has an inner diameter that is less than an outer diameter of the distal portion 60 of the coupler 58, and thus is held in place via compressive forces. In some embodiments multiple attachment methods are used.

In various embodiments, a conductor member (e.g., a conductor coil, not shown) is secured to the proximal portion 64 of the coupler 58, and extends proximally through the lead body 22 and the connector assembly 40 (see FIG. 2). In such embodiments, the coupler 58 provides an electrical connection between the conductor member and the fixation helix 24. In the connector assembly 40, the conductor member is coupled to the terminal pin 48 (see FIG. 2) such that rotation of the terminal pin 48 causes the conductor member, the coupler 58 and the fixation helix 24 to rotate. In other embodiments, the fixation helix 24 is rotated via a stylet that is inserted through an aperture that may be formed within the terminal pin 48. The distal assembly 42 is configured so that relative rotation of the coupler 58 and fixation helix 24 relative to the housing 50 results in longitudinal translation of the coupler 58 and fixation helix 24 relative to the housing 50, thereby providing the extendable/retractable functionality of the fixation helix 24. It is emphasized, however, that the particular arrangement illustrated for facilitating extension and retraction of the fixation helix 24 is exemplary only. In other words, any arrangement, whether now known or later developed, for providing the extendable/retractable functionality of the fixation helix 24 can be utilized in connection with the various embodiments.

FIG. 3 illustrates the distal assembly 42 of the present invention, which includes the fixation helix 24 having the distal biodegradable portion 29, at least a portion of which comprises a biodegradable material. The term "biodegradable" material is meant to include materials capable of being degraded by hydrolytic or enzymatic reactions typical to the anatomic site, as well as bioresorbable materials that can be broken down by the body and that do not require mechanical removal. The biodegradable portion 29 may be degraded by enzymatic processes or hydrolytic processes, for example. The biodegradable portion 29 may comprise any suitable biodegradable or bioresorbable material, including polymers and/or metals. Exemplary suitable materials include magnesium alloys, polyglycolide, polylactide, and polydioxanone. The biodegradable or bioresorbable material may have various degradation or resorption rates depending on the desired rate for use in lead 14. In various embodiments, the degradation of the biodegradable portion 29 takes place about one to two weeks after implantation, but other durations of degradation are also contemplated. The biodegradable or bioresorbable portion 29 may further comprise a therapeutic material or drug that elutes over time having a desirable effect on surrounding cardiac tissues. The therapeutic material may be, for example, a steroid or other anti-inflammatory agent.

The remainder of the fixation helix 24, i.e., the non-degradable portion 31, comprises a non-biodegradable or non-bioresorbable material that may be chosen from materials commonly used to form conventional fixation helixes or helical electrodes for implantable leads, such as those described herein, or another suitable material. As shown in FIG. 3, the embodiment allows for the biodegradable portion 29 and at least a portion of the non-degradable portion 31 to extend outside or distal to the housing 50 of the distal assembly 42.

The biodegradable portion 29, in the embodiment shown in FIG. 3, comprises a tissue-piercing or sharp tip 35 at its distal-most point. The sharp tip 35 and length of coil is desired for immediate fixation purposes, and to be able to pierce tissue during implantation. However, a sharp tip may irritate tissue (e.g., myocardium, epicardium, pericardium) and may cause inflammation and increase sensing and stimulating thresholds.

According to the various embodiments, the sharp tip 35, after a given amount of time after implantation, may then degrade, or be resorbed or dissolved leaving behind a less sharp end portion (e.g., a blunt end portion), which may minimize trauma to tissue that could result from the motion of an implanted, sharp helix tip during dynamic cardiac cycles. This could reduce chronic tissue irritation, and decrease threshold increases caused by tissue trauma or irritation. The less sharp, or blunt, end portion may also reduce possible acute penetrations or perforations into the pericardial space and possible lead body migration through the heart wall.

The biodegradable portion 29 may be attached or connected to the remainder of the fixation helix 24 (including the more proximal non-degradable portion 31) at an interface or junction 33. The interface or junction 33 may be formed by any known or future developed techniques. The technique chosen may depend upon the materials chosen to comprise the portions 29, 31 of the fixation helix 24. Some exemplary methods of joining portions 29 and 31 include, but are not limited to, welding, overmolding, mechanical joining, chemical joining or a Micro-Electro-Mechanical Systems (MEMS) technique.

In FIG. 3, dimensions of the fixation helix 24 and its components or parts are indicated with letters A, B, C, D and L. L indicates the longitudinal length of fixation helix 24 that extends outside of, or exterior to, the housing 51 when the fixation helix 24 is in its fully extended orientation, position, or configuration. Length L may range from about 0.025 inches (0.635 mm) to about 0.150 inches (3.81 mm). Lengths A and B together make up length L. Length A corresponds to the longitudinal length of the biodegradable portion 29 of the fixation helix 24, and may range from about 0.005 inches (0.127 mm) to about half the length of L. Length B corresponds to the longitudinal length of the non-degradable portion 33 that remains after the biodegradable portion 35 degrades, and may range from about half the length of L to about 0.145 inches (3.68 mm). Length B will provide a sufficient number of turns of the fixation helix 24 in order to maintain the lead 14 in the heart tissue after the biodegradable portion 29 has degraded. Distance C indicates the diameter of the fixation helix 24, and may range from about 0.025 inches (0.635 mm) to about 0.075 inches (1.91 mm). Distance D is diameter of the wire or material that is coiled to form the helix 24, and may range from about 0.005 inches (0.127 mm) to about 0.020 inches (0.508 mm).

The aforementioned lengths provided above are exemplary only. Depending upon the desired location of the fixation helix 24, such as an atrium or a ventricle, or the patient's unique cardiac pathophysiology, the various values for the dimensions A, B, C, D and/or L may vary from those specifically provided herein.

There are various embodiments of the interface 33 between the biodegradable portion 29 and the non-degradable portion 31. The embodiment of interface or junction 33 used results in certain shapes of distal ends of the non-biodegradable portion 31 that are left in place after degradation of the biodegradable portion 29.

Figure 4A:
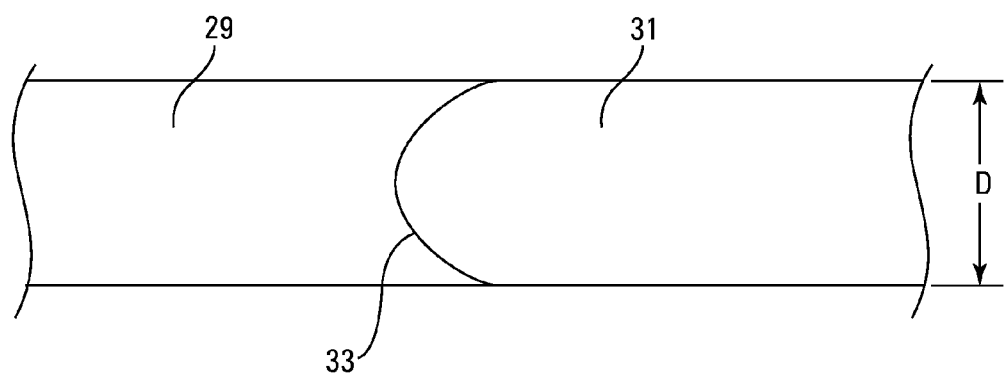
FIGS. 4A-4D are alternative enlarged, cross-sectional views of the lead of FIG. 3 at F.

FIG. 4A illustrates a cross-section of part of fixation helix 24 indicated by F in FIG. 3. The junction 33 includes a convex, rounded end on the non-degradable portion 31, and a complementary concave end on the biodegradable portion 29. After degradation of the biodegradable portion 29, a convex, rounded distal end of the fixation helix 24 is left behind. The junction 33 may be formed between the biodegradable portion 29 and non-degradable portion 31 in this embodiment using, for example, welding techniques.

Figure 4B:
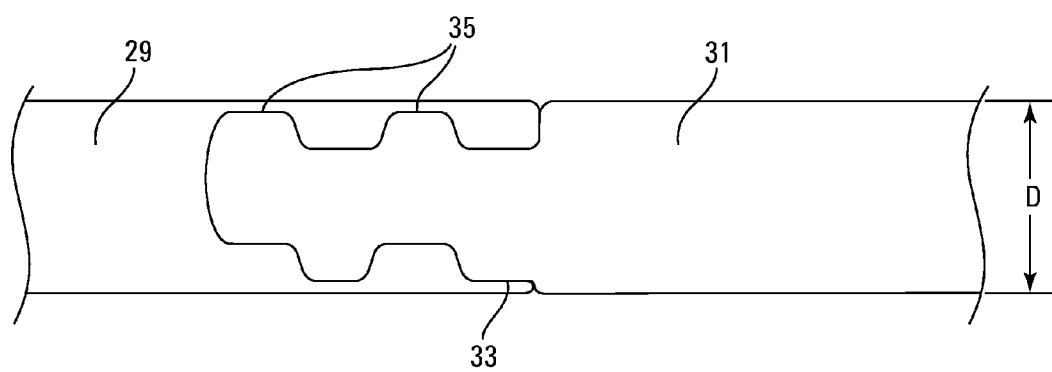

FIG. 4B illustrates another possible cross-section of fixation helix 24 indicated by F in FIG. 3. The junction 33 includes a generally male-shaped non-degradable portion 31 that includes threads 35, and a complementary female-shaped biodegradable portion 29. After degradation of the biodegradable portion 29, therefore, a threaded distal end of the fixation helix 24 is left behind. The threads 35 left behind on the non-degradable portion 31 may advantageously serve to attach to heart tissue.

The embodiment shown in FIG. 4B may be made in various ways. For example, the biodegradable portion 29 and the non-degradable portion 31 may be made separately and then threaded together. The threads 35, in the embodiment, hold the two portions 29, 31 together. An alternative method of making the embodiment shown in FIG. 4B would be to overmold the biodegradable portion 29 onto the non-degradable portion 31. In such an embodiment, for example, relief between threads 35 and non-threaded material could serve to lock or attach the portions 29, 31 together.

Figure 4C:
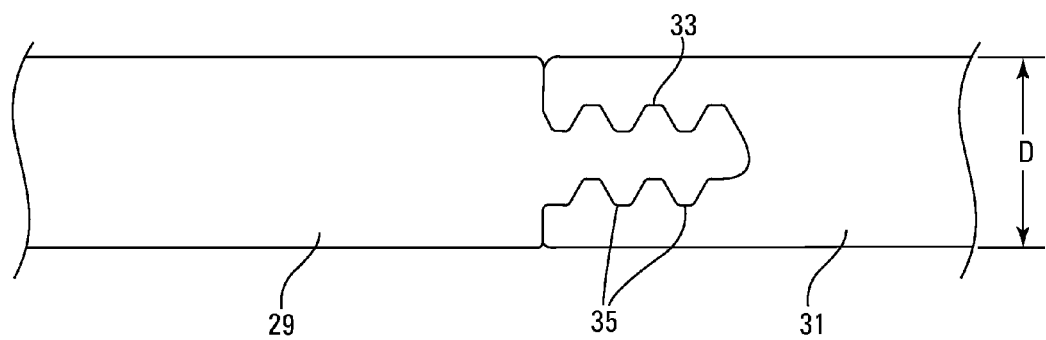

FIG. 4C illustrates another possible cross-section of fixation helix 24 indicated by F in FIG. 3. The junction 33 includes a male-shaped biodegradable portion 29 that includes threads 35, and a complementary female-shaped non-degradable portion 31. After degradation of the biodegradable portion 29, therefore a female-shaped distal end with interior threads 35 is left behind.

Figure 4D:
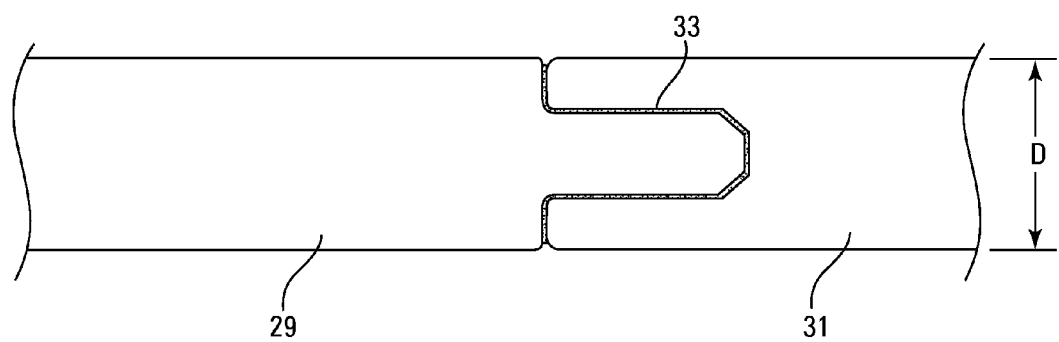

FIG. 4D illustrates yet another possible cross-section of fixation helix 24 indicated by F in FIG. 3. The junction 33 includes a female-shaped non-degradable portion 31, and a complementary male-shaped biodegradable portion 29. The non-degradable and biodegradable portions 29, 31 are bonded or attached using, for example, adhesive along the junction 33. After degradation of the biodegradable portion 29, the degradable portion 31 is left behind.

Figure 5:
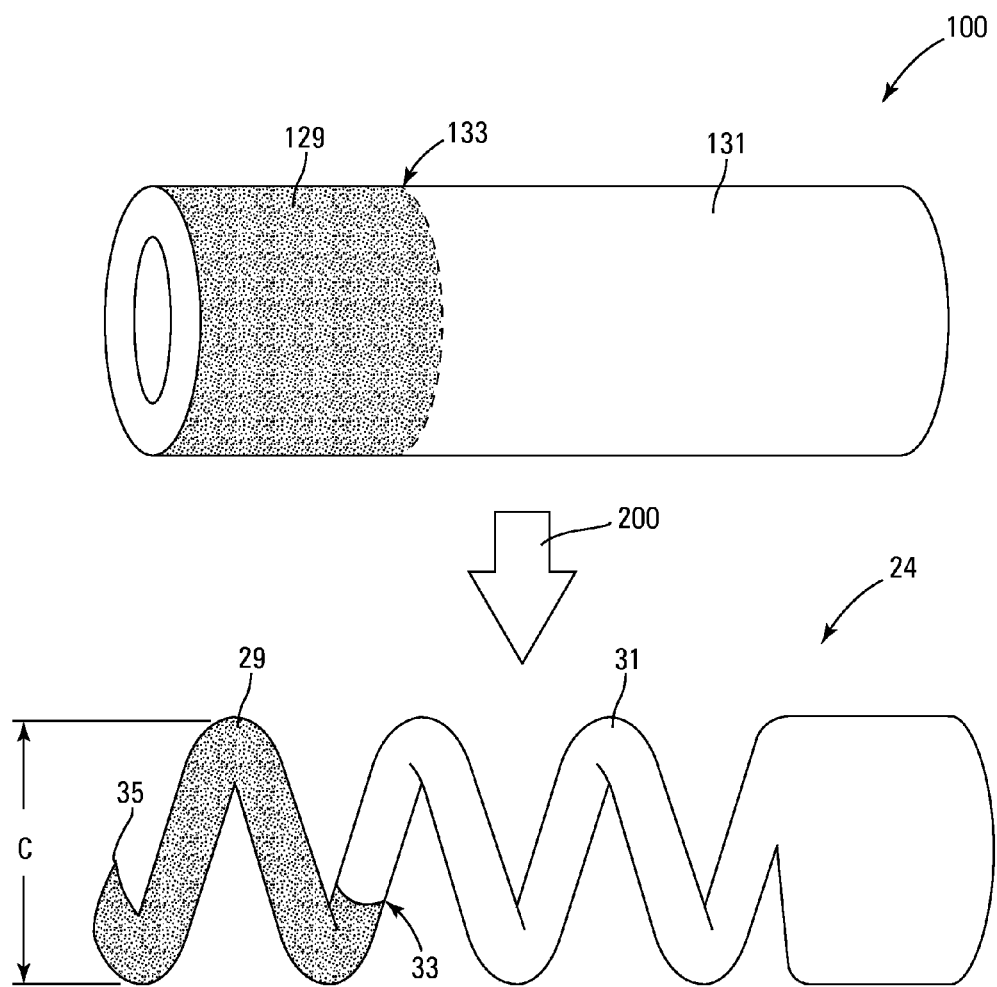
FIG. 5 shows two steps in a method of making a fixation helix that may be included in the lead of FIG. 1.

Several methods may be used to make the fixation helix 24 of the lead of the present application. In one embodiment, the biodegradable portion 29 and the remainder of the fixation helix 24 could be joined in wire form before the helix 24 is wound, resulting in helix 24. In another embodiment, as shown in FIG. 5, a tube 100 made of a biodegradable material portion 129 could be welded at a weld 133 to a non-degradable material portion 131. The tube 100 could then be laser cut (laser cut process indicated by arrow 200) to form fixation helix 24. The sharp tip 35 could be cut after the portions 29, 31 are laser cut from tube 100. In yet another embodiment, the biodegradable portion 29 and the non-degradable portion 31 could be formed separately having a helical shape, and then could be attached afterwards.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical device comprising:
   a housing having a distal end and a proximal end;
   a coupler rotatably disposed within the housing, the coupler having a proximal end and a distal end; and
   a helical electrode fixedly secured to the distal end of the coupler and configured with the coupler to translate relative to the housing between fully extended and fully retracted positions, the helical electrode comprising:
   a proximal axial length portion that comprises a non-degradable material having a first surface;
   a distal axial length portion that comprises a biodegradable material having a second surface that is complementary to the first surface; and
   an interface between the biodegradable material and the non-degradable material including the first surface and the second surface, wherein the second surface comprises a convex surface and the first surface comprises a concave surface that is complementary to the convex surface.

2. The implantable medical device of claim 1, wherein the helical electrode is configured to sense electrical activity of a patient's heart.

3. The implantable medical device of claim 1, wherein the helical electrode is configured to apply a stimulating pulse to a patient's heart.

4. The implantable medical device of claim 1, wherein the helical electrode is configured such that the biodegradable portion extends beyond the distal end of the housing when the helical electrode is fully extended.

5. The implantable medical device of claim 4, wherein the helical electrode is configured such at least a portion of the non-biodegradable portion of the helix extends beyond the distal end of the housing when the helical electrode is extended.

6. The implantable medical device of claim 4, wherein the portion of the helical electrode that extends exterior and distal to the housing, when the helical electrode is fully extended, has a length of about 0.025 inches to about 0.150 inches.

7. The implantable medical device of claim 6, wherein the distal axial length portion of the helical electrode has a length of about 0.005 inches to about half of length of the portion of the helical electrode that extends exterior and distal to the housing, and the proximal axial length portion has a length of about half of the length of the portion of the helical electrode that extends exterior and distal to the housing to about 0.145 inches.

8. The implantable medical device of claim 1, wherein the distal axial length portion comprises a portion configured to penetrate tissue.

9. The implantable medical device of claim 8, wherein the portion configured to penetrate tissue comprises a sharp distal tip for penetrating tissue.

10. The implantable medical device of claim 8, wherein the portion configured to penetrate tissue comprises a blunt distal end.

11. The implantable medical device of claim 1, wherein the second surface and the first surface are bonded together by an adhesive.

12. The implantable medical device of claim 1, wherein either one or both of the proximal axial length portion and the distal axial length portion is electrically conductive.

13. The implantable medical device of claim 1, wherein the either one or both of the proximal axial length portion and the distal axial length portion comprises an electrically conductive material including at least one of ELGILOY™, MP35N™, tungsten, tantalum, iridium, platinum, titanium, palladium, and stainless steel.

14. The implantable medical device of claim 1, wherein the housing comprises a non-electrically conductive material.

15. An implantable medical device comprising:
    a housing having a distal end and a proximal end;
    a coupler rotatably disposed within the housing, the coupler having a proximal end and a distal end; and
    a helical electrode fixedly secured to the distal end of the coupler and configured with the coupler to translate relative to the housing between fully extended and fully retracted positions, the helical electrode comprising:
    a proximal axial length portion that comprises a non-degradable material; and
    a distal axial length portion that comprises a biodegradable material; and wherein one of the distal end of the proximal axial length portion and the proximal end of the distal axial length portion comprises a plurality of threads, and the other of the distal end of the proximal axial length portion and the proximal end of the distal axial length portion comprises a surface that is complementary to the threads.

16. The implantable medical device of claim 15, wherein the distal end of the proximal axial length portion comprises the plurality of threads and the proximal end of the distal axial length portion comprises the surface that is complementary to the threads.

17. The implantable medical device of claim 15, wherein the proximal end of the distal axial length portion comprises the plurality of threads and the distal end of the proximal axial length portion comprises the surface that is complementary to the threads.

18. An implantable medical device comprising:
a housing having a distal end and a proximal end;
a coupler rotatably disposed within the housing, the coupler having a proximal end and a distal end; and
a helical electrode fixedly secured to the distal end of the coupler and configured with the coupler to translate relative to the housing between fully extended and fully retracted positions, the helical electrode comprising:
 a proximal axial length portion that comprises a non-degradable material; and
 a distal axial length portion that comprises a biodegradable material; and
wherein one of the distal end of the proximal axial length portion and the proximal end of the distal axial length portion comprises a male-shaped engagement member comprising a threaded portion, and the other of the distal end of the proximal axial length portion and the proximal end of the distal axial length portion comprises a female-shaped engagement member comprising a threaded portion, wherein the threaded portions secure the male-shaped engagement member and the female-shaped engagement member together.

19. The implantable medical device of claim 18, wherein the distal end of the proximal axial length portion comprises the male-shaped engagement member and the proximal end of the distal axial length portion comprises the female-shaped engagement member.

20. The implantable medical device of claim 18, wherein the proximal end of the distal axial length portion comprises the male-shaped engagement member and the distal end of the proximal axial length portion comprises the female-shaped engagement member.

* * * * *